(12) United States Patent
Pylyp (10) Patent No.: US 8,858,477 B2
(45) Date of Patent: Oct. 14, 2014

(54) SEPTAL SPLINT

(75) Inventor: George Steven Pylyp, Riverside, CT (US)

(73) Assignee: Arion Devices, LLC, Riverside, CT (US)

( * ) Notice: Subject to any disclaimer, the term of this patent is extended or adjusted under 35 U.S.C. 154(b) by 388 days.

(21) Appl. No.: 12/803,811

(22) Filed: Jul. 8, 2010

(65) Prior Publication Data

US 2012/0010647 A1  Jan. 12, 2012

(51) Int. Cl.
*A61F 5/00* (2006.01)
*A61F 9/00* (2006.01)
*A61F 5/08* (2006.01)

(52) U.S. Cl.
CPC ........................ *A61F 5/08* (2013.01)
USPC ................... 602/5; 602/17; 128/858

(58) Field of Classification Search
USPC ............. 602/5, 6, 17; 128/858, 857; 606/199, 606/204.45
See application file for complete search history.

(56) References Cited

U.S. PATENT DOCUMENTS

| | | | |
|---|---|---|---|
| 2,202,748 A | 5/1940 | Solo | |
| 2,274,997 A * | 3/1942 | Thurman | 128/858 |
| 2,509,157 A | 5/1950 | Lind | |
| 2,757,665 A | 8/1956 | Tanikawa | |
| 3,349,771 A | 10/1967 | Baer | |
| 3,935,859 A | 2/1976 | Doyle | |
| 4,378,802 A * | 4/1983 | Ersek | 606/157 |
| 4,592,357 A | 6/1986 | Ersek | |
| 5,094,233 A * | 3/1992 | Brennan | 602/6 |
| 5,665,104 A * | 9/1997 | Lee | 606/199 |
| 5,713,839 A * | 2/1998 | Shea | 602/17 |
| 5,983,898 A | 11/1999 | Doyle | |
| D468,826 S | 1/2003 | Doyle | |

* cited by examiner

*Primary Examiner* — Victoria J Hicks
(74) *Attorney, Agent, or Firm* — Lev Ivan Gabriel Iwashko (57) ABSTRACT

Provided is a septal splint to promote healing and alignment of a user's septum, and a method thereof. The septal splint includes an alignment member including a plurality of bilateral support pads to contact left and right sides of the user's septum, and a plurality of medializing support floor pads to rest on a bottom portion of each of the user's nasal passages. The septal splint also includes a pressing member, including a plurality of pressure applicators to transfer a predetermined amount of pressure to the bilateral support pads such that an alignment of the user's septum, maxillary crest, and fibrous tissue therebetween, is maintained, and a fulcrum end to supply the predetermined pressure to the plurality of pressure applicators. The septal splint promotes healing and alignment of a user's septum by providing moderate pressure at a junction point of the patient's maxillary crest, septum base, and fibrous tissue therebetween.

13 Claims, 13 Drawing Sheets

SEPTAL SPLINT

BACKGROUND

1. Field

The following description relates to a septal splint to promote healing and alignment of a user's septum, and a method thereof, and more particularly, to a septal splint to promote healing and alignment of a user's septum by providing moderate pressure at a junction point of the patient's maxillary crest, septum base, and fibrous tissue therebetween, and a method thereof.

2. Description of Related Art

Otolaryngology is a branch of medicine specializing in diagnosing and treating ear, nose, and throat disorders. Currently, Otolaryngologists use a conventional procedure called septoplasty to improve a patient's breathing. The conventional procedure of septoplasty is generally done by shaving (i.e., removing, scoring, transplanting, etc.) a portion of the patient's nasal septum to improve an alignment of a cartilaginous central wall, as well as peripherally, altering turbinate structures within the patient's nasal cavities.

Presently, a conventional peri-operative procedure to encourage septum alignment and to maintain unobstructed nasal pathways during healing is to insert individual silicon or plastic splints in each nostril, which are often stitched at the end closest to the nostrils using sutures, and which are then transfixed through the newly altered septum. Although the above conventional peri-operative procedure helps to dissuade edema and bleeding within the nasal cavity, the conventional methods of septum alignment do not offer necessary uniform pressure in assisting an aligned healing of the septum.

The above conventional peri-operative procedure could also introduce additional trauma to the septum which has just been altered, by way of a suture, that risks potential perforation of the septum. More specifically, at the base of the septum, where through fibrous tissue the septum is healing to the bone structure of the maxillary crest, a tacking suture may be used to tether the septum down to a base of the user's pyriform aperture while healing occurs. Without lateral inward support, there is a tendency for the inherent memory of the cartilage to re-deviate the septum. Further, there is strain on the fibrous tissue that is binding the septum and maxillary crest, challenging the aligned healing of the septum. Additionally, the use of a suture carries with it the risks of extrusion or necrosis, which is when localized cells die from some outside trauma or lack of oxygen.

After a user undergoes a septoplasty, the use of conventional individual nasal splints and transfixion stitches attempt to maintain airway space, and the fusion (i.e., placement) of the septum within the surrounding cartilage and the bone structures. The above conventional devices are focused on preventing nasal passage adhesion, in order to maintain nasal cavities and passages while disallowing a fusion of tissue across the passages in the healing process. However, the above conventional devices and methods do not include a bi-pronged splint that applies pressure to the healing area, especially at the base of the septum, of fibrous tissue and assists in the alignment of the septum, while dissuading adhesion of the nasal passages to each other after surgery, maintaining airways in the nasal cavities.

Accordingly, there is a need for a device and method to effectively promote a healing process and alignment of a patient's septum after a surgery, while providing comfort to the patient. Also, there is a need for a device and method to facilitate a healing of a stretched mucoperichondrium by offering moderate pressure at a 'fusion point' between the maxillary crest and the septum.

SUMMARY

In one general aspect there is provided a septal splint to be inserted in a user's nasal passages to maintain alignment of the user's septum, reduce tension on healing fibrous tissue, and maintain placement with the user's maxillary crest, including an alignment member, including a plurality of bilateral support pads to contact left and right sides of the user's septum, and a plurality of medializing support floor pads to rest on a bottom portion of each of the user's nasal passages, and a pressing member, including a plurality of pressure applicators to transfer a predetermined amount of pressure to the bilateral support pads such that an alignment of the user's septum, maxillary crest, and fibrous tissue therebetween, is maintained, and a fulcrum end to supply the predetermined pressure to the plurality of pressure applicators.

The bilateral support pads may include inner portions to contact the user's septum and outer portions to contact the pressure applicators and receive the predetermined pressure therefrom.

The septal splint may further include a plurality of splint spines to be disposed between the pressure applicators and the outer portions of each of the bilateral support pads, and to evenly distribute the predetermined pressure to the bilateral support pads.

The bilateral support pads may be made of a first material, and the splint spines may be made of a second material that is harder, more dense, or more durable than the first material.

The pressing member may further include a plurality of triggers to allow the bilateral support pads to be separated from each other by increasing a distance between the pressure applicators.

The triggers may be disposed between the fulcrum end and the pressure applicators, and may include at least one of a spring, a horseshoe shaped clip, a magnet, and a button.

The predetermined pressure may be based on a predetermined elasticity of the pressing member.

The bilateral support pads may be altered in shape and size to fit inside the user's nasal passages.

The medializing support floor pads may be concave to coincide with curvatures of the nasal passages, to medialize the septal splint and the septum, to decrease stress on the fibrous tissue, and to prevent re-deviation of the septum.

The bilateral support pads may further include insertion tips to be first inserted into the user's nasal passages.

The predetermined pressure may decrease gradually from the pressure applicators toward the insertion tips.

The septal splint may further include bent parts to be bent at a predetermined angle to allow the fulcrum end to contact the user's philtrum to maintain stability of the septal splint.

In another general aspect, there is provided a septal splint to be inserted in a user's nasal passages to maintain alignment of the user's septum, reduce tension on healing fibrous tissue, and maintain placement with the user's maxillary crest, including a plurality of bilateral support pads to contact left and right sides of the user's septum, a plurality of pressure applicators to transfer a predetermined amount of pressure to the bilateral support pads such that an alignment of the user's septum, maxillary crest, and fibrous tissue therebetween, is maintained, and at least one trigger to increase a distance between the bilateral support pads.

The septal splint may further include a plurality of medializing support floor pads to rest on a bottom portion of each of the user's nasal, passages.

The septal splint may further include a fulcrum end to supply the predetermined pressure to the plurality of pressure applicators, such that the predetermined pressure is based on an elasticity of the fulcrum end.

In another general aspect, there is provided a method of aligning a user's septum, reducing tension on healing fibrous tissue, and maintaining placement with the user's maxillary crest, including maintaining a concave shape of the user's nasal passages using a plurality of medializing support floor pads resting on a bottom portion the user's nasal passages, supplying a predetermined pressure from a fulcrum end to a plurality of pressure applicators, and transferring the predetermined pressure from the plurality of pressure applicators to a plurality of bilateral support pads contacting left and right sides of the user's septum, such that an alignment of the user's septum, maxillary crest, and fibrous tissue therebetween, is maintained.

Other features will become apparent to those skilled in the art from the following detailed description, which, taken in conjunction with the attached drawings, discloses exemplary embodiments.

BRIEF DESCRIPTION OF THE DRAWINGS

Throughout the drawings and the detailed description, unless otherwise described, the same drawing reference numerals will be understood to refer to the same elements, features, and structures. The elements may be exaggerated for clarity and convenience.

DETAILED DESCRIPTION

The following detailed description is provided to assist the reader in gaining a comprehensive understanding of the methods, apparatuses and/or systems described herein. Accordingly, various changes, modifications, and equivalents of the systems, apparatuses and/or methods described herein will be suggested to those of ordinary skill in the art. Also, description of well-known functions and constructions are omitted to increase clarity and conciseness.

Figure 1:
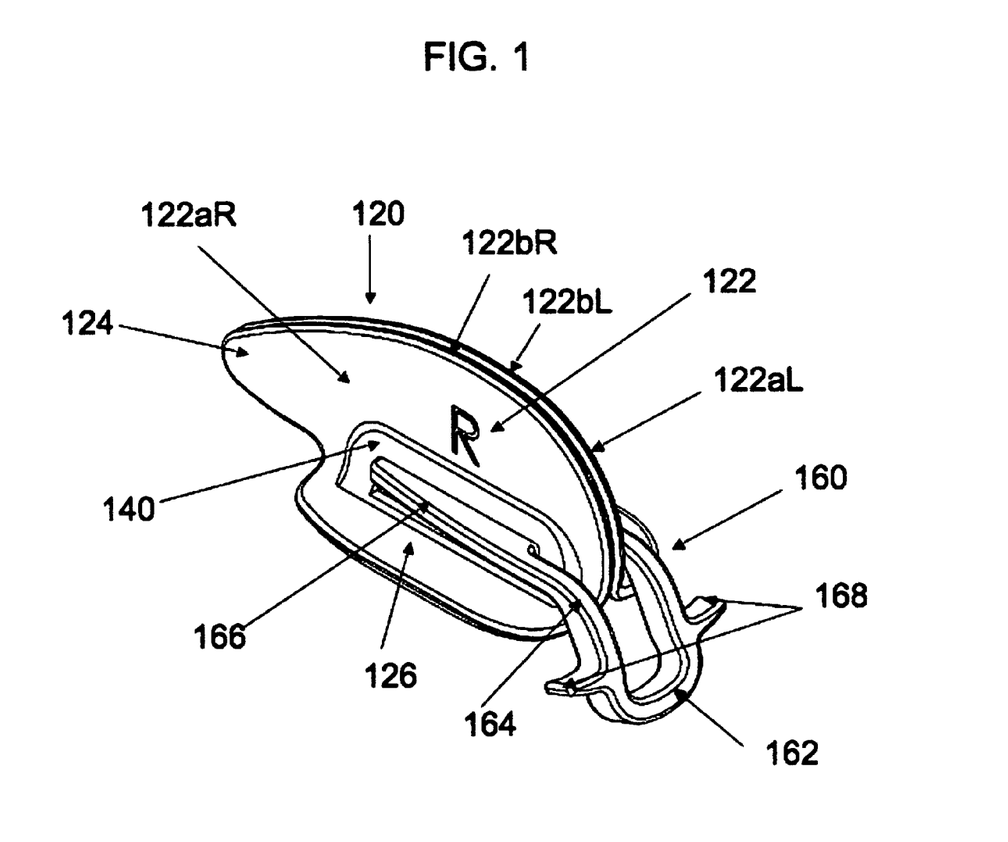
FIG. 1 is a diagram illustrating an example of angled left top view of a septal splint.
Figure 2:
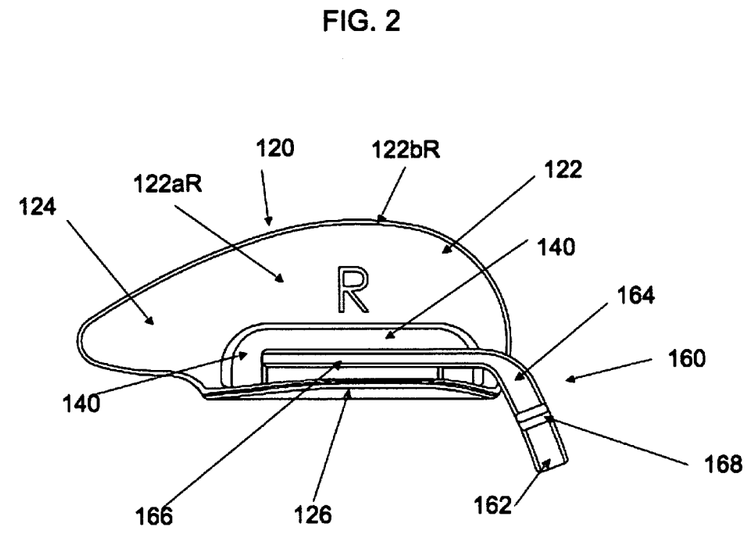
FIG. 2 is a diagram illustrating an example of a left side view of a septal splint.
Figure 3:
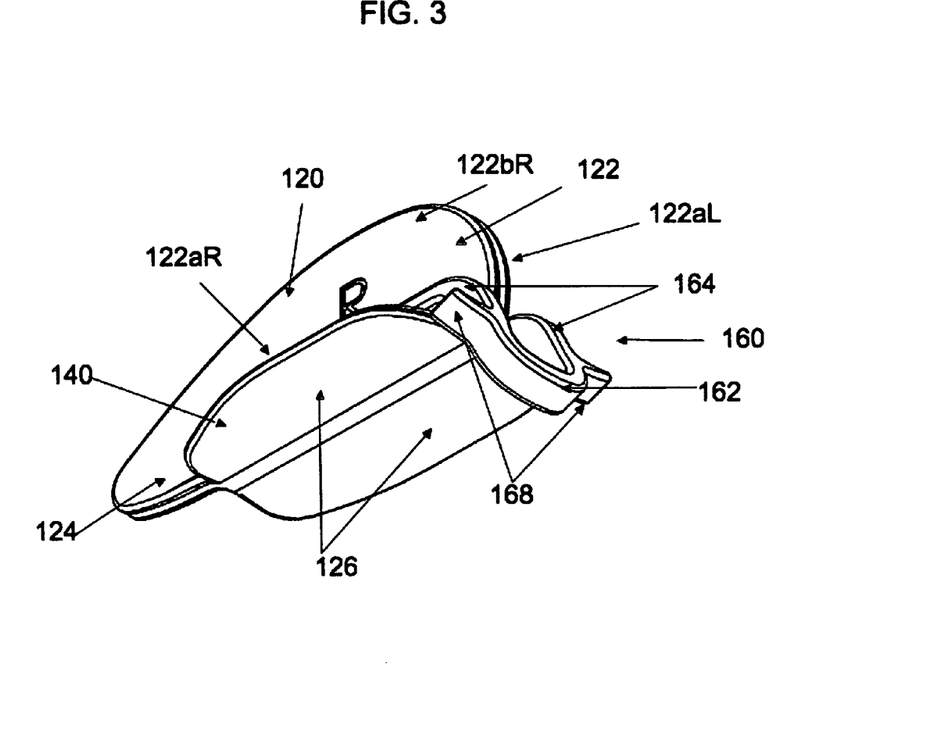
FIG. 3 is a diagram illustrating an example of an angled left bottom view of a septal splint.
Figure 4:
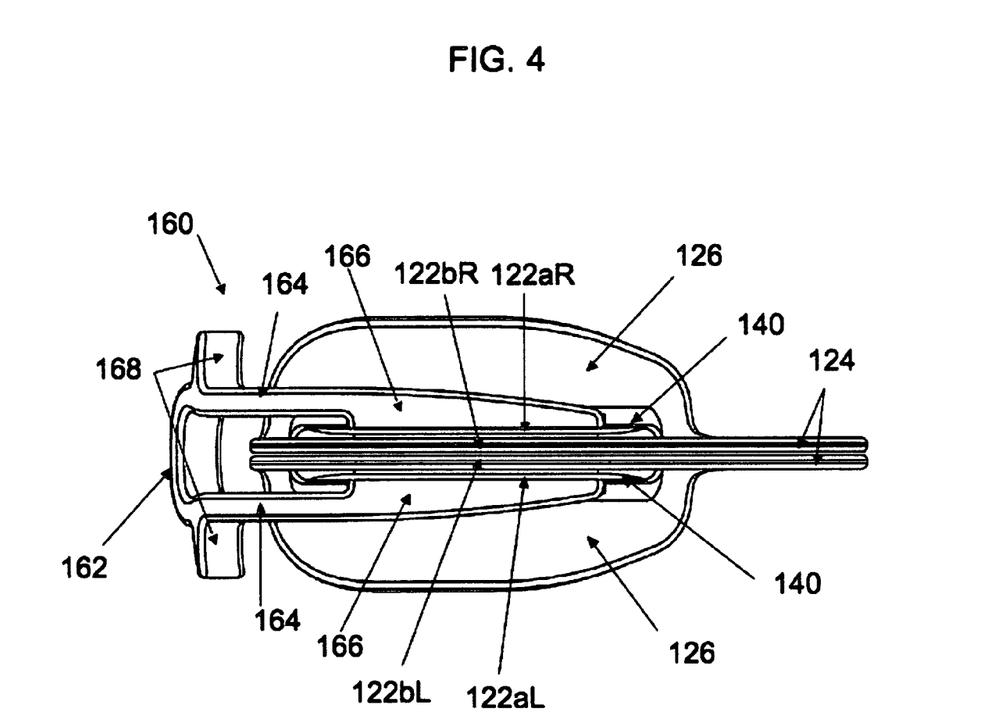
FIG. 4 is a diagram illustrating an example of a top view of a septal splint.
Figure 5:
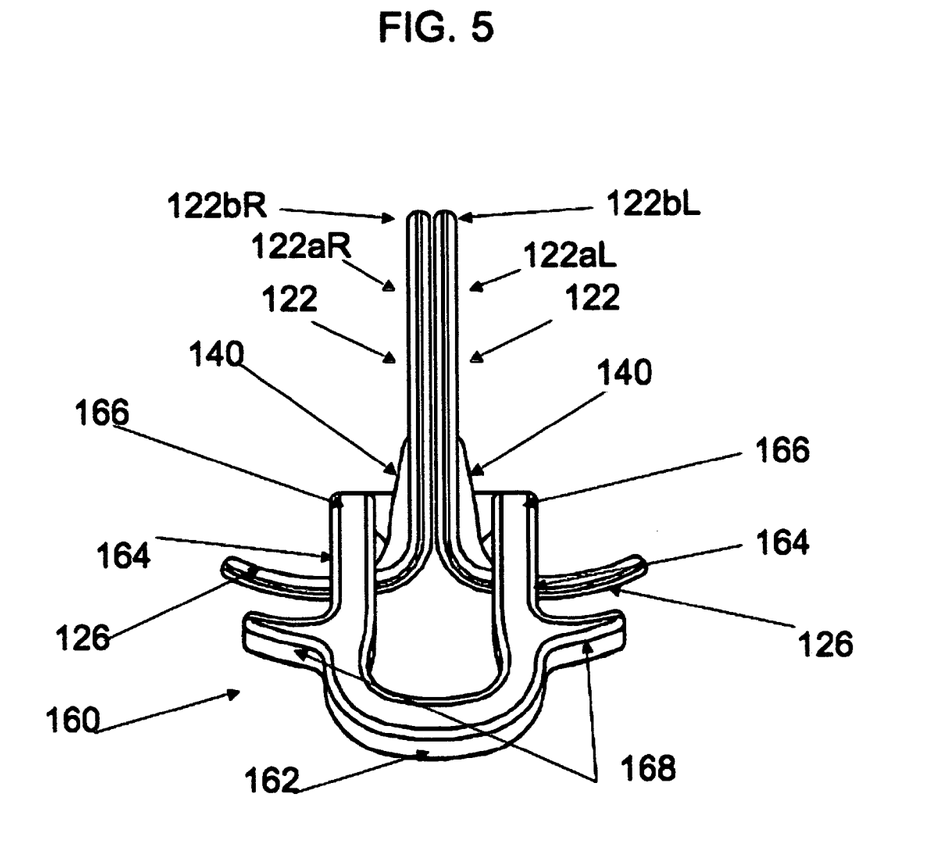
FIG. 5 is a diagram illustrating an example of a front view of a septal splint.
Figure 6:
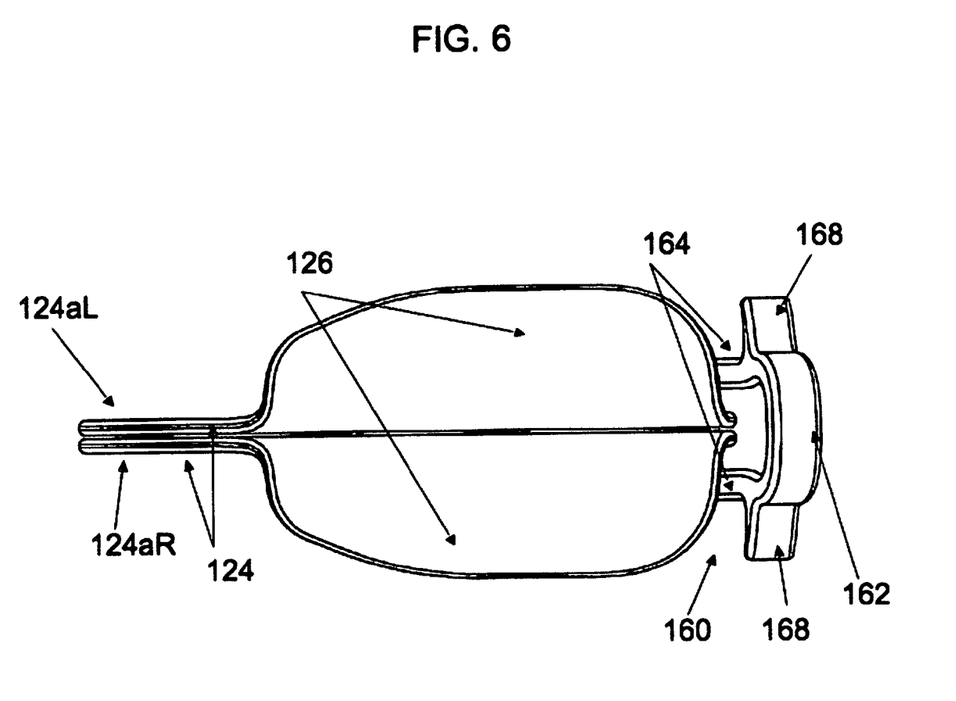
FIG. 6 is a diagram illustrating an example of a bottom view of a septal splint.
Figure 7:
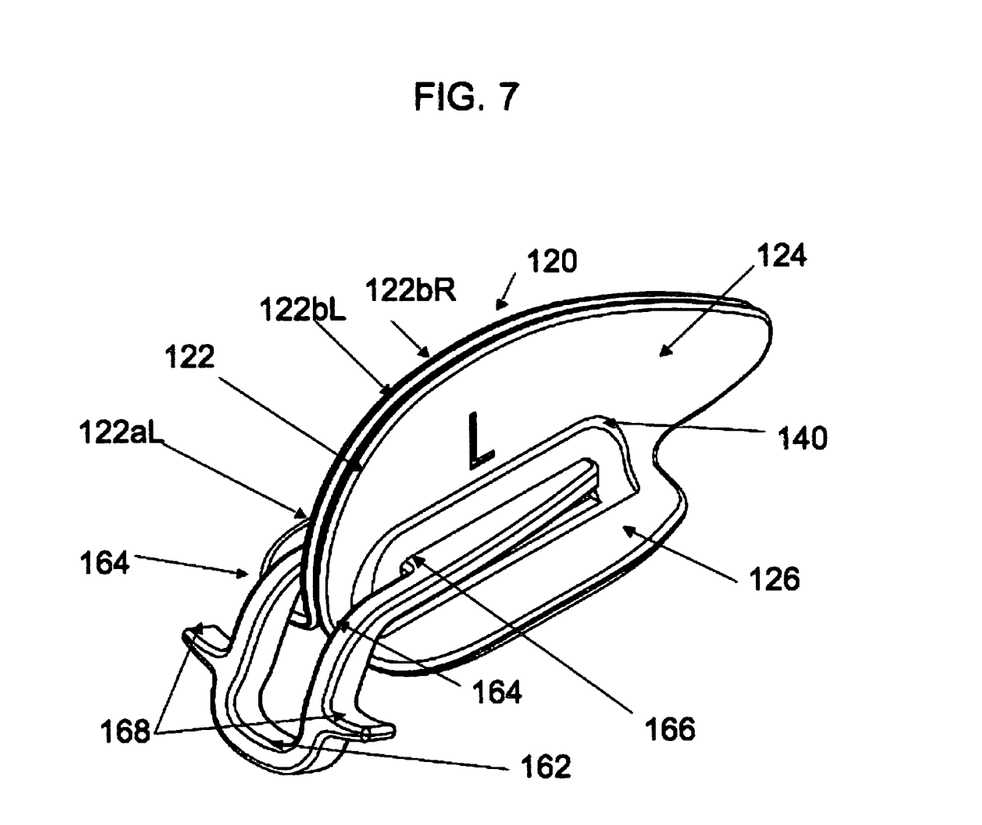
FIG. 7 is a diagram illustrating an example of an angled right top view of a septal splint.
Figure 8:
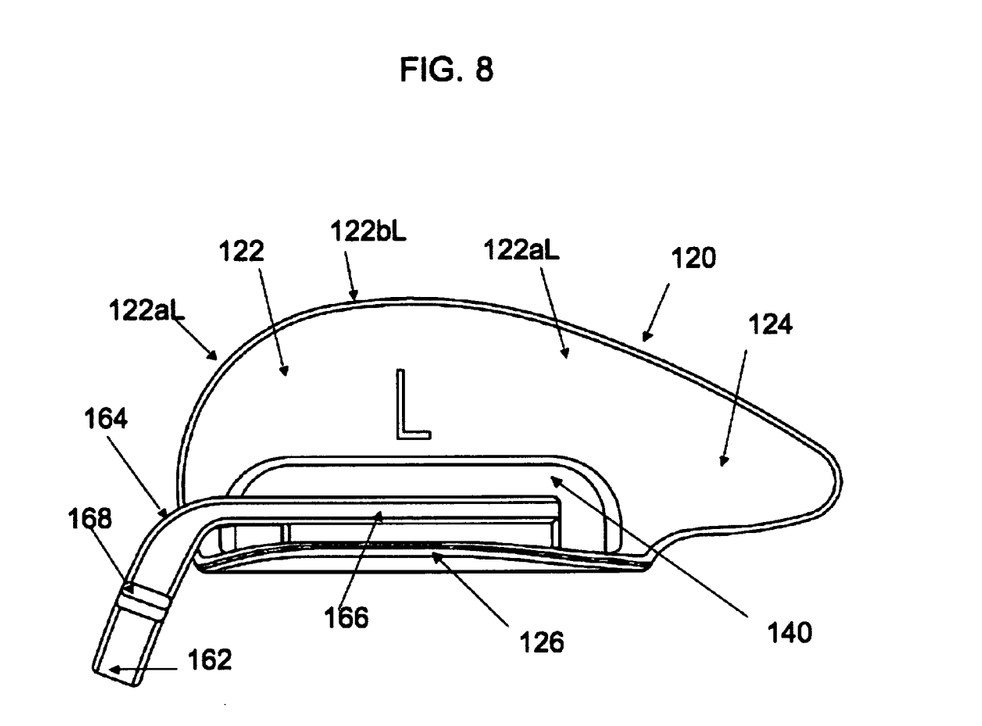
FIG. 8 is a diagram illustrating an example of a right side view of a septal splint.
Figure 9:
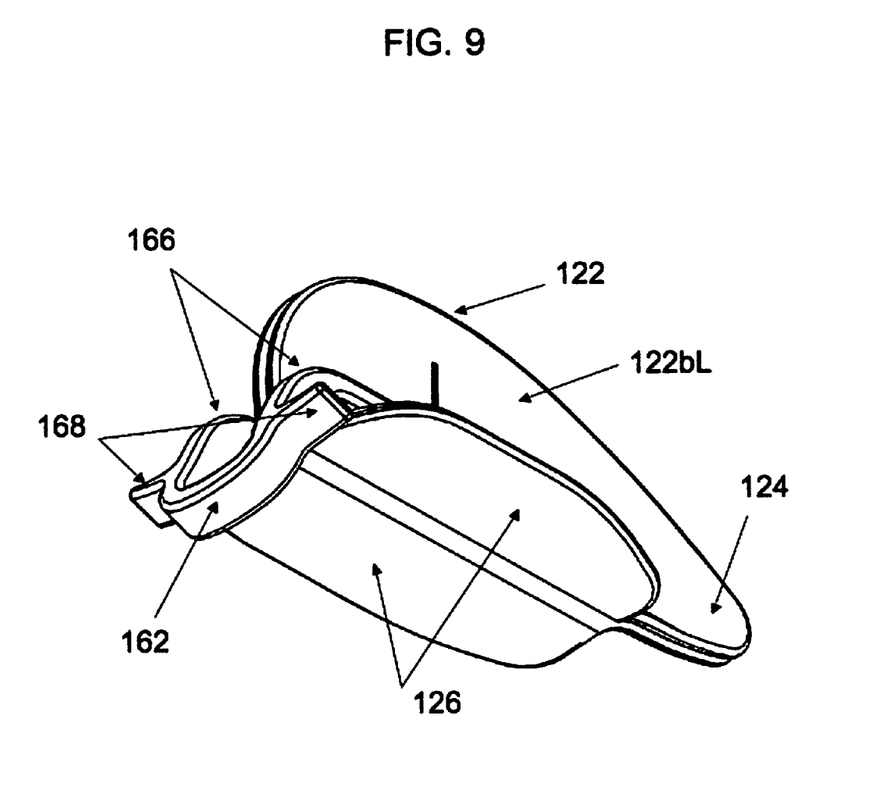
FIG. 9 is a diagram illustrating an example of an angled right bottom view of a septal splint.
Figure 10:
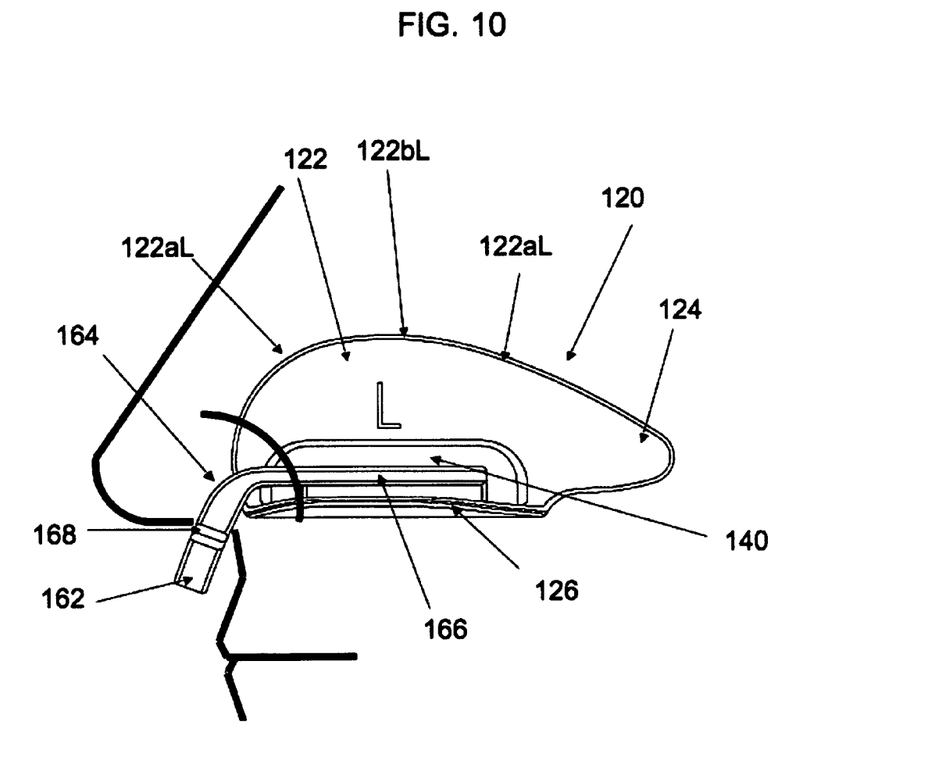
FIG. 10 is a diagram illustrating an example of a right side view of a septal splint within a user's nasal passages.
Figure 11:
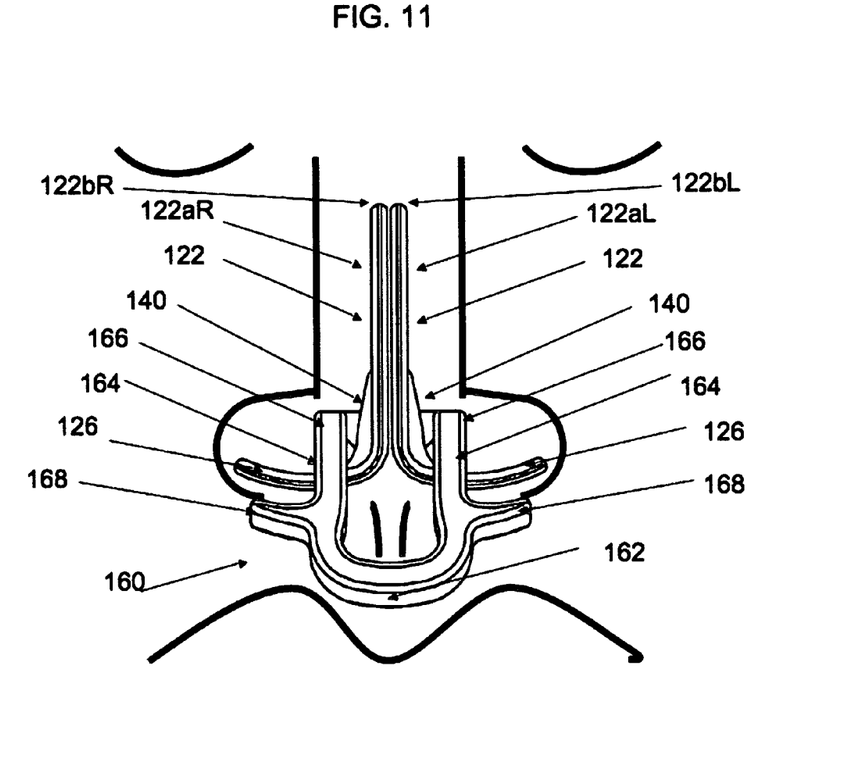
FIG. 11 is a diagram illustrating an example of a front view of a septal splint within a user's nasal passages.

FIG. 1 illustrates an angled left top view of a septal splint 100. The septal splint 100 may be made entirely of individual elements or combinations thereof, including but not limited to, silicone, plastics, polymers, metals, wood, synthetics, glass, etc.

The septal splint 100 includes an alignment member 120 and a pressing member 160. The alignment member 120 and the pressing member 160 may be made of any material known to one of ordinary skill in the art, including but not limited to, silicone, plastics, polymers, metals, wood, synthetics, glass, etc. Also, the alignment member 120 and the pressing member 160 may be made of different materials, or may be made from the same material.

The alignment member 120 is divided into two halves to allow insertion into a user's left and right nasal passages, and includes bilateral support pads 122, insertion tips 124, and medializing (a.k.a., centering) support floor pads 126.

The pressing member 160 includes a fulcrum end 162, bent parts 164, and pressure applicators 166. The pressing member may also include triggers 168.

Referring to FIGS. 1 through 12, the septal splint 100 may be inserted into a user's nasal passages by the insertion tips 124, until only the pressing member 160 is visible outside the user's nasal passages. The user may insert the nasal splint 100 into the user's nasal passages until the bilateral support pads 122 are fully inserted into the user's nasal passages, and at least until the bent parts 164 reach the user's nasal passage openings.

The bilateral support pads 122 extend upwards and laterally along the user's mucoperichondrial flaps. The bilateral support pads 122 may be cut, shaped, or molded to fit more comfortably within the user's nasal passages. Referring to FIGS. 1 through 3 and FIGS. 7 through 9, the bilateral support pads 122 may be labeled L and R to designate into which of the user's nasal passages each respective bilateral support pad 122 is to be inserted.

Referring to FIGS. 1 through 9, the bent parts 164 may be bent at a predetermined angle to allow the fulcrum end 162 to contact a user's philtrum to maintain stability of the septal splint 100, but neither the bent parts 164 nor the fulcrum end 162 are limited thereto. For example, fulcrum end 162 may not always contact the philtrum, but may be outside and around the user's columella.

After the alignment member 120 is fully inserted into the user's nasal passages, a right inner support pad portion 122$a$R (designated with an "R" in FIG. 1) and a left inner support pad portion 122$a$L (designated with an "L" in FIG. 2) of the bilateral support pads 122 press against right and left portions of the user's septum, respectively, to promote overall alignment of the user's septum. Regardless of a direction of deviation of the user's septum, the right inner support pad portion 122$a$R and left inner support pad portion 122$a$L press against the right and left sides of the user's septum with an equal pressure.

The pressure exerted on the right and left sides of the user's septum originates from the fulcrum end 162. More specifically, the pressing member 160 is designed to have a predetermined elasticity, and the fulcrum end 162 transfers a predetermined pressure based on the predetermined elasticity to the pressure applicators 166. Accordingly, the pressure applicators 166 transfer the predetermined pressure to a right outer support pad portion 122$b$R and a left outer support pad portion 122$b$L.

Referring to FIGS. 1 through 9, the septal splint 100 may also include splint spines 140 to be disposed between the pressure applicators 160 and each of the bilateral support pads 122. More specifically, splint spines 140 may be disposed between the right outer support pad portion 122bR and the left outer support pad portion 122bL, respectively.

The splint spines 140 may be made of a material that is more durable or more dense than the bilateral support pads 122, in order to withstand the predetermined pressure exerted by the pressure applicators 166, to evenly distribute the predetermined pressure along the bilateral support pads 122, and to withstand pressure exerted by a tendency of septal re-deviation during the healing process. For example, the splint spines 140 may be made from a more durable material including but not limited to, silicone, plastics, metals, wood, synthetics, glass, etc. Referring to FIGS. 1 through 9, the pressure applicators 166 may transfer the predetermined pressure first to the durable splint spines 140, which then evenly distribute the predetermined pressure to the right outer support pad portion 122bR and the left outer support pad portion 122bL, respectively.

Referring to FIGS. 1 through 11, the predetermined pressure exerted by the pressure applicators 166 allows the bilateral support pads 122 to maintain a constant force at a junction point of the user's septum, fibrous tissue, and maxillary crest. Accordingly, the constant force at the junction point of the user's septum, fibrous tissue, and maxillary crest allows the user's septum to retain post-surgical alignment during the healing process. Also, the predetermined pressure provides moderate pressure and/or support along the sides of the septum and along interiors of the user's nasal passages in supporting surrounding tissue and mucoperichondrial healing. Furthermore, the predetermined pressure exerted by the pressure applicators 166 on the user's septum prevents the tendency of septal redeviation during the healing process.

The predetermined elasticity of the fulcrum end 162, and resulting predetermined pressure exerted by the pressure applicators 166, may be altered based on a user's needs. Also, the predetermined elasticity and predetermined pressure may be calculated specifically to support the user's healing process and to prevent necrosis.

The medializing support floor pads 126 rest on a base portion of the user's nasal passage, and may be concave to coincide with a curvature of the user's nasal passage. This concavity of the medializing support floor pads 126 allows a user's nasal passages to be unobstructed to allow the user to breathe easily when the septal splint 100 is inserted within the user's nasal passages. Accordingly, since oxygen is supplied normally to the user's nasal passages, the concavity of the medializing support floor pads 126 further acts to prevent necrosis. Moreover, the concavity of the medializing support floor pads 126 also prevents adhesion of the user's nasal passages.

Figure 12:
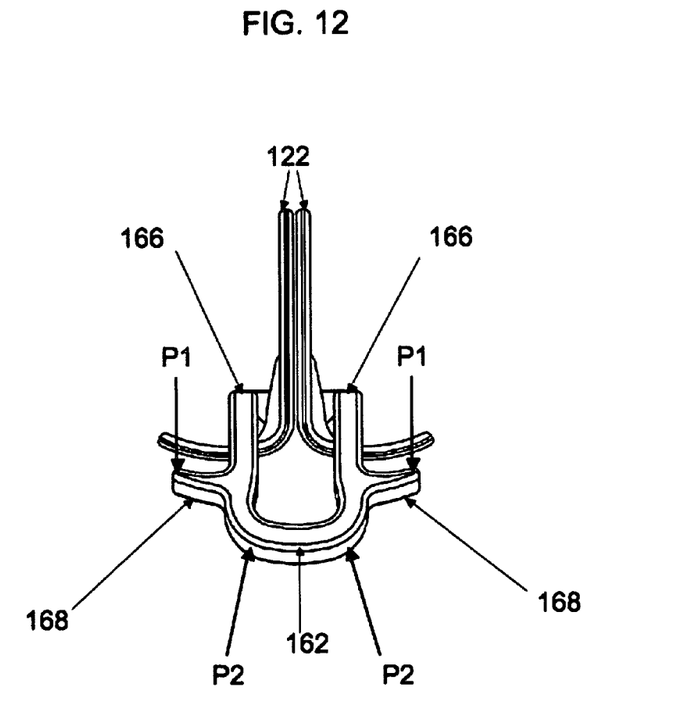
FIG. 12 is a diagram illustrating an example of how triggers function to insert or extract a septal splint into or out from a user's nasal passages.

FIG. 12 illustrates how the triggers 168 function to insert or extract the septal splint 100 into or out from a user's nasal passages.

Referring to FIG. 12, the triggers 168 may be included to facilitate an insertion of the septal splint 100 into the user's nose, or an extraction of the septal splint 100 therefrom. More specifically, the user (or physician) may apply pressure to the triggers 168 and fulcrum end 162, as illustrated by arrows P1 and P2, respectively, in order to cause a distance between the pressure applicators 166 to increase. As the distance between the pressure applicators 166 increase, a distance between the bilateral support pads 122 also increases. Accordingly, the user (or physician) can more easily and more comfortably insert or remove the septal splint 100.

The triggers 168 may include lateral protrusions, horseshoe shaped clips, magnets, springs, and buttons, but are not limited thereto. For example, the triggers 168 may include any type of programmable system, electronic system, or nano-biotechnological system to allow a user to automatically insert or extract the septal splint 100 either with or without applying manual pressure.

Figure 13:
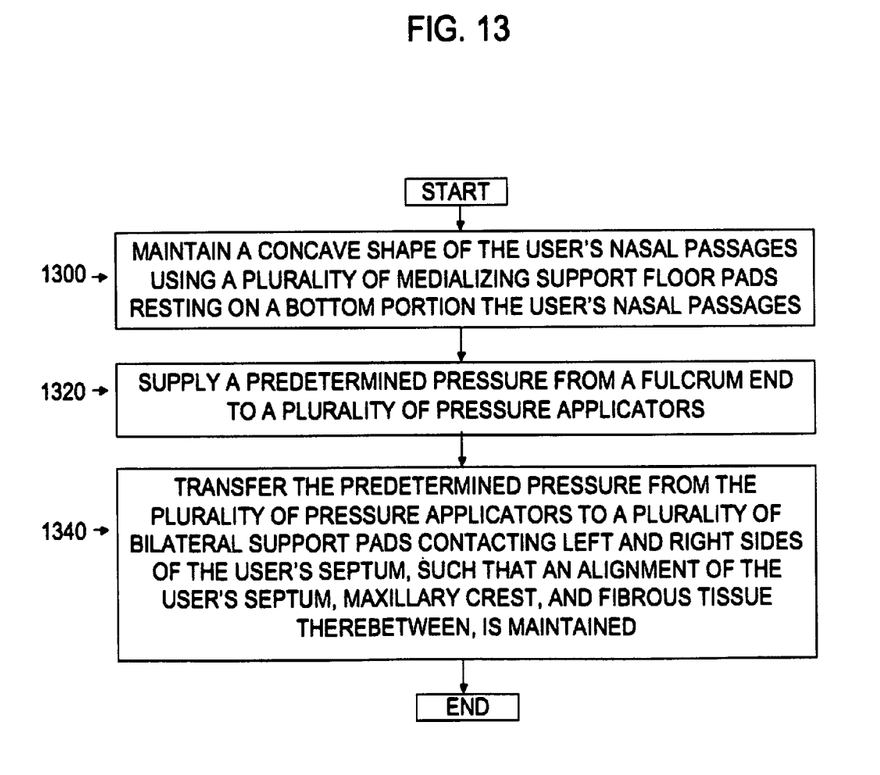
FIG. 13 is a diagram illustrating an example of a method of aligning a user's septum, reducing tension on healing fibrous tissue, and maintaining placement with the user's maxillary crest.

FIG. 13 illustrates a method of aligning a user's septum, reducing tension on healing fibrous tissue, and maintaining placement with the user's maxillary crest.

Referring to FIGS. 1 through 13, at 1300, a concave shape of the user's nasal passages is maintained using a plurality of medializing support floor pads 126 resting on a bottom portion the user's nasal passages.

At 1320, a predetermined pressure is supplied from a fulcrum end to a plurality of pressure applicators 166.

At 1340, the predetermined pressure is transferred from the plurality of pressure applicators 166 to a plurality of bilateral support pads 122 contacting left and right sides of the user's septum, such that an alignment of the user's septum, maxillary crest, and fibrous tissue therebetween, is maintained.

The above-described exemplary embodiments provide a septal splint to promote healing and alignment of a user's septum, and a method thereof, and more particularly, to a septal splint to promote healing and alignment of a user's septum by providing moderate and medically appropriate pressure at a junction point of the patient's maxillary crest, septum base, and fibrous tissue therebetween, and a method thereof. In other words, the above-described embodiments of the septal splint illustrate an encouragement of medialization (symmetry and centering) of the septal splint and therefore the septum, decreasing the stress on fibrous tissue and discouraging the re-deviation of the septum during a healing process.

A number of exemplary embodiments have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A septal splint to be inserted in nasal passages of a user to maintain alignment of a septum of the user, reduce tension on healing fibrous tissue of the user, and maintain placement with a maxillary crest of the user, comprising:
   an alignment member, comprising:
      a plurality of bilateral support pads to contact left and right sides of the septum of the user, and
      a plurality of medializing support floor pads each extending only once along only a single concave arch away from a bottom of the plurality of bilateral support pads to rest on a bottom portion of each of the nasal passages of the user; and
   a pressing member, comprising:
      a plurality of pressure applicators to transfer a predetermined pressure to the plurality of bilateral support pads such that an alignment of the septum of the user, the maxillary crest of the user, and the healing fibrous tissue of the user therebetween, is maintained, and
      a fulcrum end to supply the predetermined pressure to the plurality of pressure applicators.

2. The septal splint of claim 1, wherein the plurality of bilateral support pads comprise:
   inner portions to contact the septum of the user; and
   outer portions to contact the plurality of pressure applicators and receive the predetermined pressure therefrom.

3. The septal splint of claim 2, further comprising:
a plurality of splint spines to be disposed between the plurality of pressure applicators and the outer portions of each of the plurality of bilateral support pads, and to evenly distribute the predetermined pressure to the plurality of bilateral support pads.

4. The septal splint of claim 3, wherein the plurality of bilateral support pads are made of a first material, and the plurality of splint spines are made of a second material that is harder, more dense, or more durable than the first material.

5. The septal splint of claim 1, wherein the pressing member further comprises:
a plurality of triggers to allow the plurality of bilateral support pads to be separated from each other by increasing a distance between the plurality of pressure applicators.

6. The septal splint of claim 5, wherein the plurality of triggers are disposed between the fulcrum end and the plurality of pressure applicators, and comprise at least one of a spring, a horseshoe shaped clip, a magnet, and a button.

7. The septal splint of claim 1, wherein the plurality of bilateral support pads further comprise:
insertion tips to be first inserted into the nasal passages of the user.

8. The septal splint of claim 7, wherein the predetermined pressure decreases gradually from the plurality of pressure applicators toward the insertion tips.

9. The septal splint of claim 1, wherein the predetermined pressure is based on a predetermined elasticity of the pressing member.

10. The septal splint of claim 1, wherein the plurality of bilateral support pads can be altered in shape and size to fit inside the nasal passages of the user.

11. The septal splint of claim 1, wherein the plurality of medializing support floor pads are concave to coincide with curvatures of the nasal passages of the user, to medialize the septal splint and the septum of the user, to decrease stress on the healing fibrous tissue of the user, and to prevent re-deviation of the septum of the user.

12. The septal splint of claim 1, further comprising:
bent parts that are bent at a predetermined angle to allow the fulcrum end to contact a philtrum of the user to maintain stability of the septal splint.

13. A septal splint to be inserted in nasal passages of a user to maintain alignment of a septum of the user, reduce tension on healing fibrous tissue of the user, and maintain placement with a maxillary crest of the user, comprising:
a plurality of bilateral support pads to contact left and right sides of the septum of the user;
a plurality of pressure applicators to transfer a predetermined amount of pressure to the plurality of bilateral support pads such that an alignment of the septum of the user, maxillary crest of the user, and fibrous tissue of the user therebetween, is maintained;
a plurality of medializing support floor pads each extending only once along only a single concave arch away from a bottom of the plurality of bilateral support pads to rest on a bottom portion of each of the nasal passages of the user; and
a plurality of triggers to increase a distance between the plurality of bilateral support pads.

* * * * *